United States Patent
Alard et al.

(10) Patent No.: US 10,357,439 B2
(45) Date of Patent: Jul. 23, 2019

(54) COSMETIC KIT FOR PROTECTING THE SKIN AGAINST UV RAYS

(71) Applicant: LVMH RECHERCHE, Saint Jean de Braye (FR)

(72) Inventors: Valerie Alard, Orleans (FR); Beatrice Beaufrere-Seron, Olivet (FR); Eric Perrier, Les Cotes D'arey (FR); Brigitte Noe, Orleans (FR)

(73) Assignee: LVMH RECHERCHE, Saint Jean de Braye (FR)

( * ) Notice: Subject to any disclaimer, the term of this patent is extended or adjusted under 35 U.S.C. 154(b) by 84 days.

(21) Appl. No.: 15/445,178

(22) Filed: Feb. 28, 2017

(65) Prior Publication Data
US 2017/0165159 A1  Jun. 15, 2017

Related U.S. Application Data

(62) Division of application No. 14/364,541, filed as application No. PCT/FR2012/052870 on Dec. 11, 2012, now abandoned.

(30) Foreign Application Priority Data

Dec. 14, 2011 (FR) ..................... 11 61600

(51) Int. Cl.
| | |
|---|---|
| *A61Q 17/04* | (2006.01) |
| *A61K 8/19* | (2006.01) |
| *A61K 8/34* | (2006.01) |
| *A61K 8/37* | (2006.01) |
| *A61K 8/40* | (2006.01) |
| *A61K 8/49* | (2006.01) |
| *A61K 8/04* | (2006.01) |
| *A61K 8/06* | (2006.01) |
| *A45D 34/04* | (2006.01) |
| *A45D 40/24* | (2006.01) |
| *A61K 8/25* | (2006.01) |
| *A61K 8/29* | (2006.01) |
| *A61K 8/36* | (2006.01) |
| *A61K 8/44* | (2006.01) |

(Continued)

(52) U.S. Cl.
CPC ............... *A61K 8/34* (2013.01); *A45D 34/04* (2013.01); *A45D 40/24* (2013.01); *A61K 8/0204* (2013.01); *A61K 8/046* (2013.01); *A61K 8/06* (2013.01); *A61K 8/064* (2013.01); *A61K 8/19* (2013.01); *A61K 8/25* (2013.01); *A61K 8/29* (2013.01); *A61K 8/342* (2013.01); *A61K 8/345* (2013.01); *A61K 8/361* (2013.01); *A61K 8/37* (2013.01); *A61K 8/40* (2013.01); *A61K 8/41* (2013.01); *A61K 8/442* (2013.01); *A61K 8/466* (2013.01); *A61K 8/496* (2013.01); *A61K 8/4933* (2013.01); *A61K 8/4946* (2013.01); *A61K 8/4966* (2013.01); *A61K 8/55* (2013.01); *A61K 8/585* (2013.01); *A61K 8/602* (2013.01); *A61K 8/8105* (2013.01); *A61K 8/84* (2013.01); *A61K 8/891* (2013.01); *A61K 8/92* (2013.01); *A61Q 17/04* (2013.01); *A45D 2200/25* (2013.01); *A61K 2800/30* (2013.01); *A61K 2800/88* (2013.01); *A61K 2800/884* (2013.01)

(58) Field of Classification Search
None
See application file for complete search history.

(56) References Cited

U.S. PATENT DOCUMENTS

| | | | |
|---|---|---|---|
| 2,463,264 A | 3/1949 | Charles et al. | |
| 4,077,441 A | 3/1978 | Rosen et al. | |

(Continued)

FOREIGN PATENT DOCUMENTS

| | | |
|---|---|---|
| EP | 0669323 | 8/1995 |
| FR | 2758721 | 7/1998 |

(Continued)

OTHER PUBLICATIONS

Database GNPD [Online] MINTEL; Mar. 2003, "Ultrasun Skincare", XP002680683, (1 page).

(Continued)

*Primary Examiner* — Robert A Wax
*Assistant Examiner* — Melissa S Mercier
(74) *Attorney, Agent, or Firm* — Hamre, Schumann, Mueller & Larson, P.C.

(57) ABSTRACT

The present invention relates to a method for protecting the skin against UV rays, using two cosmetic compositions for protecting against UV rays, the sun protection indices of which are different from each other, this method consisting in applying to the skin, before or during exposure to sunlight, a first composition having a certain sun protection index, and then in applying, during exposure to sunlight, onto the residual deposit of the first composition, the second cosmetic composition having a sun protection index lower than that of the first composition. This method advantageously makes it possible to not reapply the first composition, but to use a second product that is much more pleasant to use, while at the same time obtaining the level of protection afforded by the deposit of the initial first composition. The invention also relates to a sun protection kit comprising a first composition for protecting against UV rays having a sun protection index of greater than or equal to 30, and at least a second cosmetic composition for protecting against UV rays, having a sun protection index of less than or equal to 20, the two compositions being packaged separately.

8 Claims, No Drawings

(51) Int. Cl.
- *A61K 8/46* (2006.01)
- *A61K 8/55* (2006.01)
- *A61K 8/60* (2006.01)
- *A61K 8/84* (2006.01)
- *A61K 8/92* (2006.01)
- *A61K 8/02* (2006.01)
- *A61K 8/41* (2006.01)
- *A61K 8/58* (2006.01)
- *A61K 8/81* (2006.01)
- *A61K 8/891* (2006.01)

(56) References Cited

U.S. PATENT DOCUMENTS

| | | |
|---|---|---|
| 4,710,371 A | 12/1987 | Palinczar |
| 4,850,517 A | 7/1989 | Ter Stege |
| 5,585,091 A | 12/1996 | Pelzer et al. |
| 5,663,270 A * | 9/1997 | Richard .......... A61K 8/898 528/27 |
| 2010/0119464 A1 | 5/2010 | Gaudry et al. |

FOREIGN PATENT DOCUMENTS

| | | | |
|---|---|---|---|
| FR | 2933614 | 1/2010 | |
| WO | WO-0103663 A1 * | 1/2001 | ........... A61K 8/046 |

OTHER PUBLICATIONS

Database GNPD [Online] MINTEL; Jun. 2011, "Sun Spray SPF10 + After Sun Set", XP002680684 (4 pages).
Database GNPD [Online] MINTEL; Jun. 2007, "Sun Safety Kit", XP002680685 (6 pages).
Database GNPD [Online] MINTEL; Jun. 2008, "Summer Skin Travel Essentials", XP002680686 (4 pages).
Database GNPD [Online] MINTEL; Jan. 2009, "Sun Kit", XP002680687 (4 pages).
Database GNPD [Online] MINTEL; May 2009, "Self-Tanning Oil & Anti-Aging Facial Cream Set", XP002680688 (4 pages).
Database GNPD [Online] MINTEL; May 2010, "UV Special Care Set", XP002680689 (8 pages).
Database GNPD [Online] MINTEL; Jun. 2007, "Bronze Have More Fun!", XP002697248 (4 pages).
Colipa, CTFA SA, JCIA and CTHA: "International Sun Protection Factor (SPF) Test Method"; Colipa Guidelines, May 2006 (http://www.colipa.eu/publications-colipa-the-european-cosmetic-cosmetics-association, 46 pages.

* cited by examiner

COSMETIC KIT FOR PROTECTING THE SKIN AGAINST UV RAYS

The invention relates to a method for protecting the skin against ultraviolet (UV) rays, which consists in applying a first composition to the skin before or during exposure to sunlight, and then in reapplying, during exposure to sunlight, a second cosmetic composition with a sun protection index lower than that of said first composition, to prolong the protection of the skin. The invention also relates to a cosmetic kit comprising these two compositions.

PRIOR ART AND AIM OF THE INVENTION

In order to be efficiently protected against the harmful effects of ultraviolet rays (UV rays), health professionals recommend applying to the skin, prior to any exposure to sunlight, a composition containing organic UV-screening agents, which are especially liposoluble, and mineral UV-screening agents whose protection level is high, generally above a factor of 20.

Mineral UV-screening agents are UV-screening agents that are very effective against high exposures to UV since they reflect and scatter light. Liposoluble organic UV-screening agents have, for their part, high substantivity on the skin.

It is also recommended to renew the application of this composition regularly throughout the duration of the exposure to sunlight. The reason for this is that it has been found that the level of sun protection afforded by a cream or a lotion decreases over time after it is applied to the skin, especially on account of the decrease in thickness of the deposit of product brought about by friction, washing with water or soap, perspiration, or even the simple drying of the product on the skin. In practice, it is recommended to repeat the application of the product regularly, generally after about two hours, or earlier if, for example, the region of skin onto which the composition has been applied has been washed or exposed to seawater, or alternatively if the person has perspired by taking physical exercise.

Sun protection products, termed products with a high sun protection index, which are used for protection in the case of intense exposure to sunlight, generally have a relatively thick texture and unsatisfactory sensory properties on application, mainly caused by the presence of large contents of mineral UV-screening agents or of liposoluble organic UV-screening agents.

There is thus a need to improve the comfort of products with a high sun protection index while at the same time maintaining a high level of protection.

The inventors have found, surprisingly, that the prolongation and maintenance of the level of protection against ultraviolet rays, initially imparted by a first deposit of antisun product, do not mandatorily necessitate reapplying the same composition to the skin. The invention thus proposes to maintain and prolong the level of protection of the initial deposit made before exposure to sunlight, by means of the application after a certain time, usually two hours after application of the first deposit, of a second composition whose protection index is lower than that of the first composition applied. This novel method advantageously makes it possible to not reapply the first composition, but to use a second product whose texture is much more pleasant to apply to the regions of skin to be protected. The method of the invention thus makes it possible to improve the comfort of use of an antisun product with a high protection index without reducing the level of protection of the consumers skin.

It has already been proposed to combine the application of two different products for protecting the skin against UV rays.

In patent application FR 2 758 721, for example, a composition containing only UV-B screening agents is applied during the first days of exposure to sunlight until the skin begins to tan. Once the tan appears, generally after three to six days of exposure, another UV-A screening product is used. In this sun protection method, two products are not superposed one on the other in the same day. It therefore does not satisfy the need expressed above.

In patent application FR 2 933 614, it is sought to produce a film of antisun composition on the skin by extemporaneously reacting two products with each other. In this sun protection method, two products are not superposed one on the other in a consecutive manner over time, but they are mixed at the time of their application to the skin. A chemical reaction takes place when the two products are placed in contact, and leads to the formation of a supple and protective film on the surface of the skin.

DESCRIPTION OF THE INVENTION

Method

One subject of the invention is a method for protecting the skin against UV rays using two cosmetic compositions for protecting against UV rays which have different sun protection index values, this method consisting in:
  applying to the skin a first composition having a certain sun protection index,
  exposing the skin to sunlight, and then
  applying onto the residual deposit of the first composition a second cosmetic composition with a lower sun protection index than that of the first composition.

The method for protecting the skin against UV rays is preferably performed when the skin is exposed intensively to sunlight because the amount of sunshine is substantial or larger than the normal exposure of the exposed individual, and/or because the duration of exposure is longer than the average duration of exposure that the exposed individual undergoes.

The first composition may be applied just before or during the exposure to sunlight, while the second composition is applied during the exposure to sunlight to prolong the protection effects afforded by the first composition.

Prior to performing the method of the invention, the sun protection index, and preferably the sun protection factor SPF, of each of the two compositions was advantageously measured according to the same measuring method so as to be able to ensure that they do indeed have different protection index values.

Definition and Measurement of the Sun Protection Index

The level of sun protection afforded by each composition and also by the superposition of the deposits of each of the compositions may be measured by various methods known to those skilled in the art, performed in vivo or in vitro.

The sun protection index of a composition may be measured in vivo according to the sun protection factor measurement method published by Colipa, CTFA SA, JCIA and CTHA in May 2006 (on the website http://www.colipa.eu/publications-colipa-the-european-cosmetic-cosmetics-association; "International Sun Protection Factor Test Method—2006"). According to this method, the SPF of a composition is defined as the ratio between the irradiation time necessary to reach the erythema-forming threshold of the skin onto which the composition has been applied, and the time necessary to reach the erythema-forming threshold of naked skin. The method published by Colipa specifies the minimum conditions to be respected in order for the SPF measurement to be reproducible and significant. The directives especially mention what amount of composition must be applied to the skin, and which irradiation lamp should be used.

For the purposes of the invention, the "sun protection factor SPF" or "SPF" means the sun protection index of the composition measured according to this method. This sun protection factor SPF value is found on the packaging of sun protection cosmetic compositions, which is directed toward informing the consumer of the level of protection that will be afforded by applying said composition to exposed skin regions.

Other methods also exist for quantifying the level of protection afforded by a cosmetic product against UV rays, for instance the PPD (persistent pigment darkening) method, which measures the color of the skin observed two to four hours after exposure of the skin to UV-A (wavelengths from 320 nm to 400 nm). This method has been used since 1996 by the Japanese Cosmetic Industry Association (JCIA) for the UV-A labeling of products and by test laboratories in Europe and in the United States (Japan Cosmetic Industry Association—Technical Bullet—Measurement Standards for UVA protection efficacy—Issued Nov. 21, 1995 and effective as of Jan. 1, 1996). The UVAPPD protection factor (UVAPPD PF) corresponds to the ratio i) of the dose of UV-A radiation necessary for the skin covered with cosmetic composition to reach the pigmentation threshold (MPPDp) to ii) the dose of UV-A radiation necessary for naked skin to reach the pigmentation threshold (MPPDnp).

The method of the invention does not itself comprise any step of measuring the sun protection index.

For the method of the invention, prior to its use, the sun protection index of each of the two compositions is measured by the same measuring method. The level of sun protection afforded by one or other of the compositions can thus be compared and an order of application can be established as a function of the measured factors.

According to the same principle, the same measuring method was used, in the examples illustrating the invention, both to determine the sun protection index of each composition, and also to determine the level of protection resulting from the superposition of the two compositions one onto the other, after performing the method of the invention.

In the context of the invention, it is preferred to measure the level of sun protection provided by the first composition and the second composition, by using the method recommended by Colipa in 2006.

Advantageously, the sun protection index measured for the first composition, for the second composition, and also for the level of protection provided resulting from the superposition of the two compositions one onto the other, is the SPF.

However, the level of sun protection afforded by the first composition, the second composition, and also the superposition of the two compositions one onto the other may also be measured by using a variant of the method recommended by Colipa in 2006, the dose of product applied to the skin being less than or equal to 1 mg/cm$^2$, for example equal to 0.8 mg/cm$^2$. In this case, reference is no longer made to the "sun protection factor" or "SPF", but simply to the "sun protection index".

In the method of the invention, the second composition is preferably applied onto the first composition as soon as it has dried. The term "drying" means the at least partial evaporation of at least one ingredient of said first composition, once it has been applied to the skin. The application of the second composition is performed in the same day as the application of the first composition. Thus, when the first composition contains water, the water evaporates at least partially after the application of the composition to the skin, and the second composition is preferably applied onto the residual deposit of the first composition which has, at least partially dried.

The method of the invention advantageously makes it possible to prolong the level of sun protection over time by means of the application—a certain time after the application of a first composition—of a second product whose sun protection index is lower.

The method of the invention makes it possible to obtain, unexpectedly, a synergistic effect, since the superposition of the second composition onto the residual film of the first composition makes it possible to regain the initial level of protection.

The protection afforded against UV rays by the successive application of the two compositions according to the method of the invention, measured, for example, by the SPF, is greater than the sum of the protection afforded by the second composition and of the protection afforded by the residual film of the first composition. Thus, the superposition of the two compositions does not entail a simple addition of the protections generated by each composition taken individually, but indeed produces a synergistic effect that was not foreseeable by a person skilled in the art.

In the method of the invention, the two compositions are not intended to be mixed by hand prior to their application, or after their application to the skin. On the contrary, it is sought to superpose the deposits of each composition on the skin. Thus, the second composition is advantageously applied to the surface of the deposit of the first composition on the skin, and the person who applies the product does not seek—at the time of application of the second composition onto the first—to destroy the integrity of the first coat. In particular, the two compositions do not contain ingredients that are liable to chemically react together by the creation of covalent bonds.

The first composition is preferably applied in an amount sufficient to cover the surface of the skin to be protected against the effects of ultraviolet rays. The second composition is preferably applied in an amount sufficient to cover the residual deposit of the first composition.

Drying of the first composition may be performed by exposing the skin to sunlight, for a time of at least 10 minutes. The application of the second composition is preferably performed after a time of exposure to sunlight not exceeding two hours.

As a guide, it is usually recommended by experts to renew the application of an antisun product at most two hours after the first application.

The method of the invention is not directed toward prolonging the interval for reapplication of an antisun product, but toward prolonging the protection by applying, some time after the first application, a second composition whose protection index is lower. An interval of two hours between the initial application of the first composition and the application of the second composition is thus entirely compatible with the method of the invention.

The sun protection index measured after depositing the second composition superposed on the residual deposit of the first composition is advantageously at least equal to the sun protection index of the first composition.

According to the method of the invention, beyond the first reapplication of product, corresponding to the first application of the second composition onto the residual deposit of the first composition, it is entirely possible to reapply the second composition again to the region of skin to be protected so as to renew the film for protecting against ultraviolet rays.

First Composition

A deposit of the first composition advantageously has a sun protection index higher than that of the second composition, for equal amounts of compositions.

The first composition advantageously has a sun protection index higher than the sun protection index of formula A of composition below, applied to the skin or to an inert support in an equal amount (for example 2 mg/cm$^2$), the sun protection index being able to be measured by any method known to those skilled in the art.

The first composition advantageously has a sun protection index, for example a sun protection factor SPF, of greater than or equal to 30, preferably greater than or equal to 40 and more preferably greater than or equal to 50.

Formula A itself has an SPF of 30.

Reference Formula A of SPF 30

| INCI NAME | Mass % |
|---|---|
| WATER | qs 100 |
| BUTYLENE GLYCOL DICAPRYLATE/DICAPRATE | 9.8 |
| ETHYLHEXYL METHOXYCINNAMATE | 7.5 |
| DICAPRYLYL CARBONATE | 4.0 |
| BUTYLENE GLYCOL | 3.8 |
| METHYLENE BIS-BENZOTRIAZOLYL TETRAMETHYLBUTYLPHENOL | 3.5 |
| BIS-ETHYLHEXYLOXYPHENOL METHOXYPHENYL TRIAZINE | 3.0 |
| BEHENYL ALCOHOL | 2.2 |
| CAPRYLYL METHICONE | 2.0 |
| VP/EICOSENE COPOLYMER | 2.0 |
| GLYCEROL | 2.0 |
| POTASSIUM CETYL PHOSPHATE | 2.0 |
| DIMETHICONE | 2.0 |
| CETEARYL ALCOHOL | 1.2 |
| PHENYLBENZIMIDAZOLE SULFONIC ACID | 1.0 |
| TROMETHAMINE | 0.9 |
| PHENOXYETHANOL | 0.9 |
| *COCOS NUCIFERA* (COCONUT) OIL | 0.9 |
| PHENYL TRIMETHICONE | 0.8 |
| CAPRYLYL GLYCOL | 0.6 |
| DECYL GLUCOSIDE | 0.5 |
| XANTHAN GUM | 0.3 |
| CETEARYL GLUCOSIDE | 0.3 |
| SILICA | 0.2 |
| TETRASODIUM EDTA | 0.2 |
| TOCOPHERYL ACETATE | 0.2 |
| CARBOMER | 0.1 |
| COSMETIC ACTIVE AGENTS | 0.2 |

UV-Screening Agents

The first composition contains at least one UV-screening agent that may be chosen from hydrophilic organic UV-screening agents, liposoluble organic UV-screening agents and mineral UV-screening agents.

The term "hydrophilic organic UV-screening agent" means any organic compound that absorbs ultraviolet (UV) radiation in the wavelength range from 280 nm to 400 nm, which may be dissolved in the aqueous phase of the composition, or which may be dispersed therein in colloidal form or in micellar form.

Among the hydrophilic UV-screening agents, use may be made of the following UV-screening agents denoted below by their INCI name or their chemical name:

terephthalylidenedicamphorsulfonic acid (INCI name: terephthalylidene dicamphor sulfonic acid) sold under the name Mexoryl® SX by Chimex, bis-benzazolyl derivatives as described in patents EP 669 323 and U.S. Pat. No. 2,463,264 and more particularly the compound disodium phenyldibenzimidazoletetrasulfonate sold under the trade name Neo Heliopan® AP by Haarmann and Reimer, p-aminobenzoic add (INCI name: PABA) and derivatives thereof such as 1-(4-aminobenzoate)-1,2,3-propanetriol (INCI name: Glyceryl PABA) and PEG-25 PABA sold under the name Uvinul® P25 by BASF, 2-phenylbenzimidazole-5-sulfonic add (INCI name: phenylbenzimidazolesulfonic acid) sold especially under the trade name Eusolex® 232 by Merck, triethanolamine salicylate, 3-(4'-sulfobenzylidene)camphor (INCI name: benzylidenecamphorsulfonic acid) sold under the name Mexoryl® SL by Chimex, methylenebis(benzotriazolyl)tetramethylbutylphenol (USAN name: Bisoctrizole) sold under the reference Tinosorb® M or Mixxim® BB/100 by Fairmount Chemical;

3-(4'-trimethylammoniumbenzylidene)-1-bornan-2-one methyl sulfate (INCI name: camphorbenzalkoniummethosulfate) sold under the name Mexoryl SO by Chimex, Benzophenone-4 sold under the trade name Uvinul® MS40.

Use may also be made, as hydrophilic organic UV-screening agent, of organic molecules for screening out UV rays that are of lipophilic nature (dissolved or dispersed in a nonaqueous liquid) which have been made hydrophilic by adsorption onto a hydrophilic support of low particle size, such as polymer particles. An example that may be mentioned is bis-ethylhexyloxyphenol methoxyphenyl triazine, which is a lipophilic UV-screening agent adsorbed onto polymethyl methacrylate (PMMA) particles. The hydrophilic organic UV-screening agent may thus be a lipophilic organic molecule that screens out UV rays, adsorbed or absorbed onto a hydrophilic support, which may not screen out UV rays, such as an organic polymer.

It is preferred to use a hydrophilic UV-screening agent chosen from bis-ethylhexyloxyphenol methoxyphenyl triazine, benzophenone-4 and 2-phenylbenzimidazole-5-sulfonic acid, or a mixture thereof.

The first composition preferably contains liposoluble organic UV-screening agents or mineral UV-screening agents. According to one embodiment, it contains liposoluble organic UV-screening agents and mineral UV-screening agents.

The term "liposoluble organic UV-screening agent" means any organic compound that absorbs UV radiation in the wavelength range from 280 nm to 400 nm, which may be dissolved in molecular form in an oil, or may be dispersed in an oil in colloidal form or in micellar form.

The liposoluble organic UV-screening agents may be chosen especially from various families of chemical compounds. Mention may be made especially of para-aminobenzoic acid derivatives, salicylic derivatives, cinnamic derivatives, aminobenzophenones, anthranilic derivatives, dibenzoylmethane derivatives, ββ'-diphenylacrylate derivatives, benzylidenecamphor derivatives, phenylbenzotriazole derivatives, triazine derivatives, bis-resorcinyl triazine derivatives, imidazoline derivatives, benzalmalonate derivatives, 4,4-diarylbutadiene derivatives, benzoxazole derivatives and merocyanines, and mixtures thereof.

Examples of para-aminobenzoic acid derivatives are ethyl PABA, ethyl dihydroxypropyl PABA and ethylhexyl dimethyl PABA.

Salicylic derivatives are especially Homosalate sold especially under the name Eusolex HMS® by Rona/EM Industries; ethylhexyl salicylate sold especially under the name Neo Heliopan OS® by Symrise; dipropylene glycol salicylate sold especially under the name Dipsal® by Scher.

Among the cinnamate derivatives, mention may be made especially, in a nonlimiting manner, of: 2-ethylhexyl p-methoxycinnamate, isopropyl p-methoxycinnamate, isoamyl methoxycinnamate, Cinoxate (2-ethoxyethyl-p-methoxycinnamate), diethanolamine methoxycinnamate, glyceryl 2-ethylhexanoate di-p-methoxycinnamate, 4-bis(trimethylsiloxy)methylsilyl-3-methylbutyl trimethoxycinnamate.

Among the cinnamate derivatives mentioned above, use will be made more particularly of 2-ethylhexyl p-methoxycinnamate, also known as ethylhexyl methoxycinnamate or octyl methoxycinnamate (USAN name: Octinoxate) sold under the trade names Parsol MCX from the company DSM Nutritional Products and Uvinul MC 80 from the company BASF.

Among the benzophenone derivatives, mention will be made of Benzophenone-1 sold under the trade name Uvinul® 400; Benzophenone-2 sold under the trade name Uvinul D50; Benzophenone-3 or Oxybenzone sold under the trade name Uvinul® M40; Benzophenone-6 sold under the trade name Helisorb 11; and Benzophenone-8 sold under the trade name Spectrasorb® UV-24.

An aminobenzophenone is, for example, n-hexyl 2-(4-diethylamino-2-hydroxybenzoyl)benzoate sold especially under the trade name Uvinul® A+ by BASF.

Among the anthranilic derivatives, mention will be made of menthyl anthanilate sold especially under the reference Neo Heliopan® MA by Symrise.

Among the dibenzoylmethane-based UV-screening agents, mention may be made especially, in a nonlimiting manner, of: 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4,4'-dimethoxydibenzoylmethane, 4-tert-butyl-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, 2,6-dimethyl-4-tert-butyl-4'-methoxydibenzoylmethane.

Among the dibenzoylmethane derivatives mentioned above, use will be made most particularly of 4-(tert-butyl)-4'-methoxydibenzoylmethane, also known as butylmethoxydibenzoylmethane (abbreviated as BMDBM, of ICICI name 1-[4-(1,1-dimethylethyl)phenyl]-3-(4-methoxyphenyl)-1,3-propanedione and of USAN name Azobenzone) sold under the trade names Parsol® 1789 from the company DSM Nutritional Products, or Eusolex® 9020 from the company Merck.

Two β,β'-diphenylacrylate derivatives are Octocrylene, sold especially under the trade name Uvinul® N539 by BASF; and Etocrylene, sold especially under the trade name Uvinul® N35 by BASF.

Examples of benzylidenecamphor derivatives are 3-benzylidenecamphor; methylbenzylidenecamphor sold especially under the name Eusolex® 6300 by Merck; and polyacrylamidomethylbenzylidenecamphor.

A phenylbenzotriazole derivative that may be mentioned is Drometrizole trisiloxane sold especially under the name Silatrizole® by Rhodia Chimie.

Among the triazine derivatives; mention may be made of: ethylhexyl triazone sold especially under the trade name Uvinul® T150 by BASF; diethylhexylbutamidotriazone sold especially under the trade name Uvasorb® HEB by Sigma 3V; 2,4,6-tris(dineopentyl 4'-aminobenzalmalonate)-s-triazine; 2,4,6-tris(disobutyl 4'-aminobenzalmalonate)-s-triazine; 2,4-bis(dineopentyl 4'-aminobenzalmalonate)-6-(n-butyl 4'-aminobenzoate)-s-triazine; bis(ethylhexyloxyphenolmethoxyphenyl)triazine and 2,4-bis(n-butyl 4'-aminobenzoate)-6-(aminopropyltrisiloxane)-s-triazine.

A bis-resorcinyltriazine derivative is bis(ethylhexyloxyphenolmethoxyphenyl)triazine sold especially under the trade name Tinosorb® S by Ciba Geigy.

An imidazoline derivative is ethylhexyl dimethoxybenzylidene dioximidazoline propionate.

Benzalmalonate derivatives are polyorganosiloxanes bearing a benzalmalonate function such as Polysilicone-15 sold especially under the trade name Parsol® SLX by DSM Nutritional Products, Inc.; and dineopentyl 4'-methoxybenzalmalonate.

A benzoxazole derivative is 2,4-bis[5-1(dimethylpropyl)benzoxazol-2-yl(4-phenyl)imino]-6-(2-ethylhexyl)imino-1,3,5-triazine sold especially under the name Uvasorb® K2A by Sigma 3V.

A merocyanine derivative is octyl 5-N,N-diethylamino-2-phenylsulfonyl-2,4-pentadienoate.

An example of a 4,4-diarylbutadiene derivative is 1,1-dicarboxy(2,2'-di methylpropyl)-4,4-diphenylbutadiene.

In the context of the present invention, a liposoluble organic UV-screening agent is preferably chosen from the following UV-screening agents, and mixtures thereof: ethylhexyl salicylate; Octocrylene; ethylhexyl triazone; ethylhexyl methoxycinnamate; butylmethoxydibenzoylmethane; bis(ethylhexyloxyphenolmethoxyphenyl)triazine; or Oxybenzone.

The first composition may also contain at least one mineral UV-screening agent.

The mineral UV-screening agents may be chosen from metal oxide pigments with a mean particle size generally between 5 nm and 100 nm and preferably between 10 nm and 50 nm, for instance titanium oxide pigments (amorphous or crystallized in rutile and/or anatase form), iron oxide, zinc oxide, zirconium oxide or cerium oxide pigments.

The pigments may or may not be surface-treated.

The surface-treated pigments are pigments that have undergone one or more surface treatments of chemical, electronic, mechanochemical and/or mechanical nature with compounds as described, for example, in Cosmetics & Toiletries, February 1990, vol. 105, pp. 53-64, such as amino acids, beeswax, fatty acids, fatty alcohols, anionic surfactants, lecithins, sodium, potassium, zinc, iron or aluminum salts of fatty acids, metal alkoxides (of titanium or aluminum), polyethylene, silicones, proteins (collagen, elastin), alkanolamines, silicon oxides, metal oxides or sodium hexametaphosphate.

The silicones used for treating pigments are chosen, for example, from the group containing alkyl silanes, polydialkylsiloxanes and polyalkylhydrogenosiloxanes.

Needless to say, the metal oxide pigments, before being treated with silicones, may have been treated with other surface agents, in particular with cerium oxide, alumina, silica, aluminum compounds, silicon compounds, or mixtures thereof.

In the context of the invention, it is preferred to use titanium oxide in amorphous form or crystallized in rutile and/or anatase form as mineral UV-screening agent.

The content of UV-screening agent in the first composition is, for example, between 0.5% and 40% by weight, and particularly ranges from 5% to 30% by weight and more particularly from 10% to 20% by weight relative to the total weight of the composition.

The content of liposoluble UV-screening agent in the first composition is, for example, between 5% and 15% by weight, and particularly ranges from 10% to 12% by weight relative to the total weight of the composition.

The content of hydrophilic UV-screening agent in the first composition is, for example, between 1% and 10% by weight, and particularly ranges from 4% to 6% by weight relative to the total weight of the composition.

The first composition preferably contains from 0 to 5% by weight of mineral UV-screening agents, and more preferably does not contain any.

The first composition preferably contains at least one screening agent for screening out $UV_A$ and at least one screening agent for screening out $UV_B$. The term "$UV_A$" means wavelengths ranging from 315 to 400 nm, and "$UV_B$" means wavelengths ranging from 280 to 315 nm. An organic screening agent that is active in the $UV_A$ range is advantageously chosen from:
dibenzoylmethane derivatives,
menthyl anthranilate sold especially under the reference Neo Heliopan® MA by Symrise, and
mixtures thereof.

The first composition preferably comprises the following UV-screening agents, taken alone or as a mixture: 2-ethylhexyl p-methoxycinnamate, methylenebis(benzotriazolyl) tetramethylbutylphenol, bis(ethylhexyloxyphenolmethoxyphenyl)triazine, 2-phenylbenzimidazole-5-sulfonic acid.

Nonvolatile Polar Oil

The first composition preferably contains a nonvolatile polar oil which allows the dissolution of the UV-screening agent contained in the second composition.

For the purposes of the invention, the term "nonvolatile polar oil" means a water-insoluble fatty substance that is liquid at 25° C. and 0.1 MPa and nonvolatile, having a nonzero vapor pressure, at 25° C. and 0.1 MPa, of less than 2.6 Pa, preferably less than 0.13 Pa, which contains at least one and preferably at least two oxygen atoms or conjugated double bonds.

The oil is preferably chosen from aliphatic monoesters and diesters, non-hydroxylated aromatic esters, aliphatic carbonates and phenyl silicones.

Examples of polar oils that may be mentioned include
aliphatic monoesters and diesters, especially i) monoesters of a linear or branched, saturated or unsaturated, preferably saturated, aliphatic carboxylic acid, comprising from 8 to 20 carbon atoms, and of an aliphatic monoalcohol comprising from 3 to 20 carbon atoms, ii) aliphatic diesters of an aliphatic dicarboxylic acid comprising from 4 to 10 carbon atoms and of a monoalcohol,
monoesters of benzoic acid and of an aliphatic alcohol comprising from 8 to 20 carbon atoms, 2-ethylhexyl benzoate, 2-octyldodecyl benzoate, isostearyl benzoate or C12-C15 alkylbenzoate,
triesters and tetraesters such as pentaerythritol esters, especially pentaerythrityl tetraisostearate, trimethylolpropane esters, especially trimethylolpropane triisostearate, citric add esters, especially tridecyl citrate, and tridecyl trimellitate,
dialkyl carbonates in which the alkyl groups contain from 8 to 18 carbon atoms, such as dicaprylyl carbonate and bis(2-ethylhexyl) carbonate,
hydroxylated aliphatic monoesters or diesters such as i) esters of a hydroxylated aliphatic monocarboxylic or dicarboxylic acid comprising from 3 to 20 carbon atoms, and of an aliphatic monoalcohol comprising from 6 to 20 carbon atoms, for example isostearyl lactate, octyl hydroxystearate, octyldodecyl hydroxystearate, cetyl lactate, myristyl lactate or diisostearyl malate, or ii) aliphatic monoesters and diesters of polyols, in particular of dials and triols, such as esters of an aliphatic monocarboxylic acid comprising from 3 to 20 carbon atoms, and of an aliphatic did or triol comprising from 3 to 20 carbon atoms,
aromatic hydroxylated monoesters and diesters of a hydroxylated aromatic carboxylic acid and of an aliphatic monoalcohol comprising at least 10 carbon atoms,
saturated or unsaturated aliphatic alcohols containing from 8 to 26 carbon atoms, such as octyldodecanol, octyldecanol, 2-butyloctanol, 2-hexyldecanol or 2-undecylpentadecanol,
saturated or unsaturated aliphatic monocarboxylic acids containing from 7 to 29 carbon atoms, such as oleic acid, linoleic acid, linolenic acid or isostearic acid,
silicone oils comprising at least one alkoxy or phenyl group, which is pendent or at the end of a silicone chain, containing from 2 to 24 carbon atoms, especially phenyl trimethicone, phenyl dimethicones, phenyltrimethylsiloxydiphenylsiloxanes, diphenyl dimethicones, diphenylmethyldiphenyltrisiloxanes, 2-phenylethyltrimethyl siloxysilicates and polymethylphenylsiloxanes;
glycols,
aliphatic ethers comprising more than 10 carbon atoms,
triglycerides, for example sunflower oil, corn oil, soybean oil, marrow oil, grapeseed oil, sesame oil, hazelnut oil, apricot oil, macadamia oil, arara oil, castor oil, avocado oil, jojoba oil, shea butter oil, caprylic/capric acid triglycerides, glyceryl triheptanoate, glyceryl trioctanoate, glyceryl tri(2-ethylhexanoate), glyceryl triisostearate, glyceryl triisononanoate, glyceryl trimyristate or glyceryl triisopalmitate, and
mixtures thereof.

In one embodiment, it is preferable for the oil be an ester chosen from aliphatic monoesters and diesters.

According to another embodiment, the oil is a silicone oil comprising aromatic carbon-based groups.

The preferred polar oils of the first composition are C12-C15 alkylbenzoate and isodecyl neopentanoate.

Film-Forming Agents

The first composition is preferably water-resistant. In one embodiment, it contains a polymer for reinforcing the cohesiveness and the persistence of the deposit of composition on the skin and reinforces the integrity and persistence of the deposit of the composition on the skin, in particular on contact with fresh or saline water.

According to one embodiment, the first composition is in the form of an emulsion containing from 10% to 20% of antisun UV-screening agents and at least one polymer.

Film-forming polymers that may be mentioned include vinylpyrrolidone derivatives such as VP/hexadecene copolymer, VP/eicosene copolymer and tricontanyl PVP; acrylate copolymers or styrene/acrylates/ammonium methacrylate copolymers; polyurethanes of polyurethane-34 type or of polyurethane-35 type.

Emulsion

According to one embodiment, the first composition contains water, which at least partially evaporates after it has been applied to the skin. The second composition is advantageously applied onto the residual deposit of the first composition which has at least partially dried.

It is advantageously in the form of a water-in-oil or oil-in-water emulsion and preferably contains at least 20% by weight of water, more preferably at least 30% by weight of water and more preferentially from 40% to 80% by weight of water relative to the total weight of the composition. According to one embodiment, the composition contains from 45% to 50% by weight of water.

According to one embodiment, the first composition is in the form of an emulsion containing at least one liposoluble UV-screening agent.

The second composition is applied onto the first composition after at least drying the latter. When the first composition contains water, the drying of said composition on the skin corresponds to the at least partial evaporation of the water it contains.

The sun protection index of the first composition decreases over time, once it has been applied to the skin. The decrease in protection may have various causes depending on the case, such as the evaporation of the water or of the solvents it contains, the deformation of the film of composition formed on the surface of the skin or the penetration of certain compounds into the skin. This is why it is preferable to apply the second composition within an interval such that the sun protection index afforded by the first composition has not reached too low a threshold, which deprives the consumer from a sufficient, efficient and desired antisun protection.

It is consequently preferred, in the context of the present invention, for the second composition to be applied onto the deposit of the first composition as soon as the sun protection index of the first composition reaches a minimum threshold, which may be expressed as being greater than or equal to 30% of its initial value, for example equal to 35%; 40%; 45%, 50%, 55%, 60%, 65%, 70%, 75% or even 80% of its initial value. In this case, the process may be performed in accordance with the procedure described in the examples that follow.

Advantageously, the application of the second composition onto the deposit of the first is performed after a time of exposure to sunlight not exceeding 2 hours, preferably after an interval of at least 30 minutes, of at least 45 minutes, of at least one hour or of at least one hour 30 minutes, and after the application of the first composition onto the region of skin to be protected.

Advantageously also, the second composition is applied to the skin shortly after the region of skin onto which the first composition has been applied has been exposed to water, for example after swimming in the sea or taking a shower, or alternatively after physical exercise.

The first composition is preferentially intended to be applied to the face or the body and is preferably in the form of an oil-in-water or water-in-oil emulsion or an aqueous gel. The composition is, for example, in the form of a cream, a lotion, a serum or a fluid for the face, or a milk.

Second Composition

The second composition advantageously has a sun protection index that is less than or equal to the sun protection index of formula B of composition below applied to the skin or to an inert support in an equal amount (for example 2 mg/cm$^2$), the sun protection index being able to be measured by any method known to those skilled in the art.

The reference formula B itself has an SPF of 20.

Reference formula B of SPF 20

| INCI NAME | Mass % |
| --- | --- |
| WATER | 63 |
| ETHYLHEXYL METHOXYCINNAMATE | 7.5 |
| CYCLOPENTASILOXANE | 3.1 |
| GLYCEROL | 3 |
| DICAPRYLYL CARBONATE | 3 |
| PENTYLENE GLYCOL | 3 |
| BUTYLENE GLYCOL | 2 |
| BENZOPHENONE-3 | 2 |
| TITANIUM DIOXIDE | 1.8 |
| CETEARYL ALCOHOL | 1.8 |
| GLYCERYL STEARATE | 1.5 |
| PEG-100 STEARATE | 1.2 |
| OCTOCRYLENE | 1 |
| CETYL ALCOHOL | 1 |
| STEARYL ALCOHOL | 1 |
| BETAINE | 1 |
| PHENOXYETHANOL | 0.5 |
| BENZOPHENONE-4 | 0.5 |
| DIMETHICONE | 0.5 |
| CETETH-10 PHOSPHATE | 0.4 |
| DICETYL PHOSPHATE | 0.4 |
| STEARIC ACID | 0.3 |
| ACRYLATES/C10-30 ALKYL ACRYLATE CROSSPOLYMER | 0.3 |
| SODIUM HYDROXIDE | 0.2 |

The protection index of the second composition is defined in the same way as the protection index of the first composition described previously.

The second composition advantageously has a sun protection index, for example a sun protection factor SPF, of less than or equal to 20 and preferably less than or equal to 10.

The second composition advantageously has a sun protection index, for example a sun protection factor SPF, of greater than or equal to 3, preferably greater than or equal to 5 and more preferably greater than or equal to 6.

According to one embodiment, the second composition contains an organic UV-screening agent and a volatile oil, and its SPF is between 5 and 20 and preferably between 7 and 10.

UV-Screening Agents

The second composition contains at least one UV-screening agent, which may be chosen from hydrophilic organic UV-screening agents, liposoluble organic UV-screening agents and mineral UV-screening agents, and mixtures thereof.

The second composition preferably contains at least one organic UV-screening agent. It is preferably free of mineral UV-screening agents responsible for a texture with a heavier feel.

The second composition preferably contains at least one liposoluble organic UV-screening agent as defined previously.

Each composition preferably contains at least one UV-screening agent for screening out $UV_A$ and at least one UV-screening agent for screening out $UV_B$.

The content of UV-screening agent in the second composition is, for example, between 2% and 20% by weight, and particularly ranges from 4% to 15% by weight and more particularly from 10% to 15% by weight, relative to the total weight of the composition.

The second composition preferably comprises the following UV-screening agents, alone or as a mixture: diethylhexylbutamidotriazone, butylmethoxydibenzoylmethane, Octocrylene, Benzophenone-3, ethylhexyl methoxycinnamate.

Volatile Oil

The second composition preferably contains at least one volatile oil.

The volatile oil may be chosen from hydrocarbon-based oils containing from 8 to 16 carbon atoms, and especially:
- branched C8-C16 alkanes, for instance C8-C16 isoalkanes, especially isododecane (also known as 2,2,4,4,6-pentamethylheptane), isodecane and isohexadecane,
- branched C8-C16 esters, for instance isohexyl neopentanoate,
- aliphatic C2-C5 alcohols, preferably ethanol.

The volatile oil may also be chosen from linear or cyclic silicone oils, especially those with a viscosity of less than 6 centistokes, and especially containing from 3 to 6 silicon atoms, these silicones optionally comprising one or more alkyl or alkoxy groups containing 1 or 2 carbon atoms.

As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane, 3-butyl-1,1,1,3,5,5,5-heptamethyltrisiloxane, 3-propyl-1,1,1,3,5,5,5-heptamethyltrisiloxane and 3-ethyl-1,1,1,3,5,5,5-heptamethyltrisiloxane, and mixtures thereof.

Fluorinated organic solvents may also be used as volatile oil.

The volatile oil is preferably chosen from isododecane, decamethylcyclopentasiloxane (D5) and alcohol, and mixtures thereof.

The volatile oil may represent from 20% to 80% and preferably from 50% to 70% by weight relative to the total weight of the composition.

The second composition preferably contains less than 10% by weight of water and more preferably less than 5% by weight of water relative to the total weight of said composition.

According to one embodiment, it contains a high proportion of ethanol, especially more than 30%, more than 40% or even more than 50% by weight relative to the weight of the first composition, so as to afford a sensation of freshness at the time of its application onto the deposit of the first composition.

According to one embodiment, the second composition contains at least one volatile oil, is free of mineral UV-screening agent and contains less than 10% by weight of water.

Spray

The second composition is preferentially intended to be applied to the face or the body and is preferably in the form of a composition comprising less than 5% by weight of water. The composition is, for example, in the form of an oil, in particular a dry oil. The second composition may advantageously be vaporized onto the skin in the form of fine particles by means of devices suitable for spraying this type of composition. These devices, which are well known to those skilled in the art, comprise non-aerosol pumps or "atomizers", aerosol containers comprising a propellant gas. The latter are described, for example, in patents U.S. Pat. Nos. 4,077,441 and 4,850,517. The compositions packaged in aerosol form generally contain conventional propellants, for instance compressed air, hydrofluoro compounds of dichlorodifluoromethane, difluoroethane, dimethyl ether, isobutane, n-butane, propane or trichlorofluoromethane.

Kit

A subject of the invention is also a sun protection kit comprising a first composition for protecting against UV rays, containing at least one UV-screening agent and having a sun protection index of greater than or equal to 30, and at least a second cosmetic composition for protecting against UV rays, containing at least one UV-screening agent and having a sun protection index of less than or equal to 20, the two compositions advantageously being packaged separately, preferably in the same packaging.

The term "kit" means an assembly of at least two cosmetic products having different packagings and presentation forms, which are intended to be applied to the skin consecutively over time to afford protection against UV rays.

In the kit of the invention, the first composition is preferably in the form of a water-in-oil or oil-in-water emulsion, and the second composition is preferably anhydrous. The term "anhydrous" refers to a composition which contains less than 5% by weight of water.

According to one embodiment, the first composition is in the form of an emulsion and the second composition contains at least one volatile oil and less than 10% by weight of water.

According to one embodiment of the kit of the invention, the first composition has a sun protection index, for example a sun protection factor SPF, of greater than or equal to 30, preferably greater than or equal to 40, more preferably greater than or equal to 50, and the second composition has a sun protection index, for example a sun protection factor SPF, of less than or equal to 30, preferably less than or equal to 20 and even more preferentially less than or equal to 10.

Advantageously, the SPF of each of the compositions of the kit is mentioned on their packaging.

According to another embodiment of the kit of the invention, the first composition has a sun protection index greater than or equal to that of the reference formula A for equal amounts deposited on the skin, and the second composition has a sun protection index less than or equal to that of the reference formula B for equal amounts deposited on the skin.

The sun protection kit comprises, for example, a first composition in the form of a cream packaged in a tube, whereas the second is a dry oil packaged as a spray.

The characteristics of the first and second compositions described in relation with the method of the invention apply to the kit of the invention.

Advantageously, the kit according to the invention contains a written description of the sun protection method according to the invention, on the packaging or alternatively on a written support placed inside the packaging.

Use

A subject of the invention is the use of a second cosmetic composition for protecting against UV rays, for prolonging the efficacy over time of a first composition for protecting the skin against UV rays, having a sun protection index higher than that of the second composition.

A subject of the invention is also the use of a second cosmetic composition for protecting against UV rays, having a sun protection index on the skin that is lower than that of the reference formula B, for prolonging the efficacy over time of a first composition for protecting the skin against UV rays having a sun protection index greater than or equal to that of a reference formula A.

A subject of the invention is also the use of a second cosmetic composition for protecting against UV rays, having a sun protection index, for example a sun protection factor SPF, of less than 20, for prolonging the efficacy over time of a first composition for protecting the skin against UV rays having a sun protection index, for example a sun protection factor SPF, of greater than or equal to 30.

The sensory properties of the second composition are advantageously better than those of the first composition.

In particular, the second composition does not leave any greasy feel on the skin, and is glidant on application. It preferably leaves a great sensation of freshness on the skin.

The characteristics of the first and second compositions described in relation with the method of the invention apply to the use of the invention.

The invention is illustrated in greater detail by the examples that follow. In the examples, all the percentages are given on a weight basis, unless otherwise indicated, and the temperature is expressed in degrees Celsius, unless otherwise indicated, and the pressure is atmospheric pressure, unless otherwise indicated.

Example

This example relates to the results of a study consisting in evaluating the impact on the sun protection of the application of an antisun cream whose sun protection factor SPF value is equal to 50, followed by an antisun spray whose sun protection factor SPF value is equal to 8, two hours after a first application of said antisun cream.

The study was performed on ten individuals.

The compositions tested are the following:

First Composition: Sun Protection Cream of SPF 50

| INCI NAME | Mass % |
|---|---|
| WATER | 50.1 |
| BUTYLENE GLYCOL DICAPRYLATE/DICAPRATE | 10.6 |
| ETHYLHEXYL METHOXYCINNAMATE | 7.5 |
| METHYLENE BIS-BENZOTRIAZOLYL TETRAMETHYLBUTYLPHENOL | 5 |
| DICAPRYLYL CARBONATE | 4 |
| BUTYLENE GLYCOL | 3.7 |
| BIS-ETHYLHEXYLOXYPHENOL METHOXYPHENYL TRIAZINE | 3 |
| DIMETHICONE | 2 |
| CAPRYLYL METHICONE | 2 |
| VP/EICOSENE COPOLYMER | 2 |
| BEHENYL ALCOHOL | 2 |
| GLYCEROL | 2 |
| POTASSIUM CETYL PHOSPHATE | 2 |
| CETEARYL ALCOHOL | 1.2 |
| PHENYLBENZIMIDAZOLE SULFONIC ACID | 1 |
| TROMETHAMINE | 1 |
| PHENOXYETHANOL | 0.9 |

The above cream has sensory properties degraded by the presence of the screening agents required to obtain an SPF with a value equal to 50.

Second Composition: Sun Protection Oil spray of SPF 8

| INCI NAME | Mass % |
|---|---|
| ETHANOL | qs 100 |
| C12-15 ALKYL BENZOATE | 20.0 |
| CYCLOPENTASILOXANE | 8.0 |
| DIETHYLHEXYLBUTAMIDOTRIAZONE | 5.0 |
| WATER | 3.4 |
| BUTYL METHOXYDIBENZOYLMETHANE | 3.0 |
| OCTOCRYLENE | 2.0 |
| BENZOPHENONE-3 | 1.0 |
| ETHYLHEXYL METHOXYCINNAMATE | 1.0 |
| FRAGRANCE | 0.8 |

The oil composition of spray type is very easy and pleasant to apply to the skin. However, it has a low sun protection factor SPF which does not afford sufficient protection for prolonged and intense exposure to sunlight.

Protocol for Measuring the Sun Protection Indices, Including the SPF

The details of the method for measuring the sun protection factor SPF of the composition of the products applied are given below.

The protocol and the conditions for measuring the SPF are those given in the "International Sun Protection Factor Test Method—2006" method published by Colipa.

A sun protection index different from the SPF was also measured, by repeating the protocol and the conditions for measuring the SPF given in the "International Sun Protection Factor Test Method—2006" method published by Colipa, with the exception of the dose of product applied, which was chosen to be closer to the real conditions of use by consumers, equal to 0.8 mg/cm$^2$.

Two tests are performed, which differ from each other by the amount of product applied to the skin.

1—Application at 2 mg/cm$^2$.

The sun protection factor SPF value is measured for each of the two compositions. The measurement is performed 20 minutes after application, so as to allow the applied composition to dry.

| Compositions tested | SPF measured |
|---|---|
| ANTISUN CREAM | 51.8 ± 6.1 |
| ANTISUN SPRAY | 9.3 ± 0.9 |

The results obtained after performing the method of the invention are summarized in the table below.

| Step of the method of the invention | SPF measured |
|---|---|
| 1 - Application of the antisun cream | 51.8 ± 6.1 |
| Residual SPF, two hours after application | 34.1 ± 5.9 |
| 2 - Application of the antisun spray, two hours after application of the antisun cream | 51.6 ± 6.6 |

2—Application at 0.8 mg/cm$^2$.

The sun protection index value is measured according to the protocol described previously. The sun protection index measurement is performed 20 minutes after application, so as to allow the applied composition to dry.

| Compositions tested | Index measured |
|---|---|
| ANTISUN CREAM | 21.7 ± 3.4 |
| ANTISUN SPRAY | 7.8 ± 1.6 |

The results obtained after performing the method of the invention are summarized in the table below.

| Step of the method of the invention | Index measured |
|---|---|
| 1 - Application of the antisun cream | 21.7 ± 3.4 |
| Residual SPF, two hours after application | 13.2 ± 2.5 |

-continued

| Step of the method of the invention | Index measured |
|---|---|
| 2 - Application of the antisun spray, two hours after application of the antisun cream | 31.3 ± 5.2 |

A significant reduction in the residual sun protection of the antisun cream, two hours after application, was observed.

These studies made it possible to show that, under the conditions of application described in the method for measuring the SPF published by Colipa (2 mg/cm$^2$), but also under similar application conditions in which the amount of products applied is closer to the real conditions of application by users (0.8 mg/cm$^2$), the loss of protection of the cream is compensated for after two hours by the application of the spray.

Protection that is statistically higher than the simple addition of the two SPF values or of the two protection indices, respectively, is obtained.

Specifically, the sum of the SPF value of the residual deposit of the cream after two hours (34.1) and of the SPF value of the deposit of the spray (9.1) is equal to 43.4, whereas the SPF value resulting from the superposition of the two coats is equal to 51.6: the effect is indeed synergistic.

Similarly, the sum of the sun protection indices of each of the two deposits of compositions is much lower than the sun protection index of the two superposed deposits.

The two compositions of the example can constitute a kit according to the invention, advantageously sold with a description of the sun protection method according to the invention.

Thus, the consumer can protect himself efficiently and, by means of the presence of the second application, benefit from improved comfort of application.

The invention claimed is:

1. A method for protecting the skin of a person in need thereof against UV rays, said method comprising successively using two cosmetic compositions which have different sun protection index values, wherein said method comprises:
applying on the skin a first composition in the form of an emulsion containing at least one liposoluble UV-screening agent and having a sun protection factor (SPF) of more than or equal to 30, said liposoluble UV-screening agent being at least one selected from the group consisting of para-aminobenzoic acid, salicylic, cinnamic, benzophenones and aminobenzophenones, anthranillic, dibenzoylmethane, β,β'-diphenylacrylate, benzylidenecamphor, phenylbenzo-triazole, triazine, bis-resorcinyl triazine, imidazoline, benzalmalonate, 4,4-diarylbutadiene, benzoxazole and merocyanines, the content of said liposoluble UV-screening agent in the first composition ranging from 5 to 30% by weight relative to the total weight of the composition,
exposing the skin to sunlight, and then in the same day, applying, two hours after the application of the first composition, onto the residual deposit of the first composition, a second cosmetic composition containing at least one volatile oil and at least one UV-screening agent, and having a sun protection factor (SPF) less than that of the first composition, the sun protection factor (SPF) of the second composition being between 5 and 20, said at least one UV-screening agent of the second composition being at least one selected from the group consisting of diethylhexylbutamidotriazone, butylmethoxydibenzoylmethane, octocrylene, and benzophenone-3, ethylhexylmethoxycinnamate, the content of said UV-screening agent in the second composition ranging from 2 to 20% by weight relative to the total weight of the second composition,
so as to obtain a global sun protection factor (SPF) greater than the sum of the sun protection factor (SPF) of each of the two compositions.

2. The method as claimed in claim 1, wherein the first composition contains water which at least partially evaporates after its application on skin, and wherein the second composition is applied onto the residual deposit of the first composition which has at least partially dried.

3. The method as claimed in claim 1, wherein the sun protection factor (SPF) of each of the two compositions is measured according to the same measuring method.

4. The method as claimed in claim 1, wherein the second composition is applied to the skin shortly after a physical exercise or after that the region of skin, which the first composition has been applied onto, has been exposed to water.

5. The method as claimed in claim 1, wherein the second composition is free of mineral UV-screening agent and contains less than 10% by weight of water.

6. The method as claimed in claim 1, wherein the first composition has a sun protection factor (SPF) of more than or equal to 40.

7. The method as claimed in claim 1, wherein the second cosmetic composition has a sun protection factor (SPF) of less than or equal to 10 and more than or equal to 5.

8. The method as claimed in claim 1, wherein the first composition is a cream made of oil-in-water or water-in-oil emulsion, and wherein the second composition is a spray further comprising ethanol.

* * * * *